(12) United States Patent
Fujimoto (10) Patent No.: US 11,430,130 B2
(45) Date of Patent: Aug. 30, 2022

(54) IMAGE PROCESSING METHOD AND COMPUTER-READABLE RECORDING MEDIUM HAVING RECORDED THEREON IMAGE PROCESSING PROGRAM

(71) Applicant: SCREEN Holdings Co., Ltd., Kyoto (JP)

(72) Inventor: Hiroki Fujimoto, Kyoto (JP)

(73) Assignee: SCREEN Holdings Co., Ltd.

( * ) Notice: Subject to any disclaimer, the term of this patent is extended or adjusted under 35 U.S.C. 154(b) by 0 days.

(21) Appl. No.: 16/979,928

(22) PCT Filed: Nov. 29, 2018

(86) PCT No.: PCT/JP2018/043983
§ 371 (c)(1),
(2) Date: Sep. 11, 2020

(87) PCT Pub. No.: WO2019/181072
PCT Pub. Date: Sep. 26, 2019

(65) Prior Publication Data
US 2021/0012509 A1  Jan. 14, 2021

(30) Foreign Application Priority Data

Mar. 19, 2018 (JP) .............................. JP2018-050932

(51) Int. Cl.
*G06T 7/194* (2017.01)
*G01N 33/483* (2006.01)
(Continued)

(52) U.S. Cl.
CPC ......... *G06T 7/194* (2017.01); *G01N 33/4833* (2013.01); *G06T 3/40* (2013.01);
(Continued)

(58) Field of Classification Search
CPC . G06T 2207/30024; G06T 2207/10016; G06T 2207/30004; G06T 7/194;
(Continued)

(56) References Cited

U.S. PATENT DOCUMENTS

| 2002/0051580 A1 | 5/2002 | Yamada et al. ............... 382/239 |
| 2010/0142807 A1* | 6/2010 | Yasuda ................ G06K 9/4642 382/164 |

(Continued)

FOREIGN PATENT DOCUMENTS

| JP | H02016682 A | * | 1/1990 |
| JP | 2004-229097 A | | 8/2004 |

(Continued)

OTHER PUBLICATIONS

Segmentation of Regions in JPEG Compressed Medical Images (Year: 2004).*

(Continued)

*Primary Examiner* — Nizar N Sivji
(74) *Attorney, Agent, or Firm* — Ostrolenk Faber LLP (57) ABSTRACT

An image processing method that includes obtaining an original image including a cultured cell image with a background image, dividing the original image into blocks, each composed of a predetermined number of pixels, and obtaining a spatial frequency component of an image in each block for each block, and classifying each block as the one belonging to a cell cluster corresponding to the cell or the one belonging to other than the cell cluster in a two-dimensional feature amount space composed of a first feature amount which is a total of intensities of low frequency components having a frequency equal to or lower than a predetermined frequency and a second feature amount which is a total of intensities of high frequency components having a higher frequency than the low frequency compo- (Continued)

nent, and segmenting the original image into an area occupied by the blocks classified as the cell cluster and another area.

9 Claims, 6 Drawing Sheets

(51) Int. Cl.
  *G06T 3/40* (2006.01)
  *G06V 20/69* (2022.01)
(52) U.S. Cl.
  CPC .......... *G06V 20/695* (2022.01); *G06V 20/698* (2022.01); *G06T 2207/20021* (2013.01); *G06T 2207/20052* (2013.01); *G06T 2207/20101* (2013.01); *G06T 2207/30024* (2013.01)
(58) Field of Classification Search
  CPC ............. G06T 3/40; G06T 2207/20021; G06T 2207/20052; G06T 2207/20101; G06T 7/168; G06T 7/11; G01N 33/5035; G01N 33/4833; G06K 9/0014; G06K 9/00147
  See application file for complete search history.

(56) References Cited

U.S. PATENT DOCUMENTS

| | | | |
|---|---|---|---|
| 2015/0111291 A1* | 4/2015 | Aragaki | G06K 9/0014 435/288.7 |
| 2017/0003490 A1 | 1/2017 | Sueki et al. | |
| 2017/0337691 A1* | 11/2017 | Lim | G06T 7/11 |
| 2018/0369820 A1* | 12/2018 | Kaneko | C12M 23/12 |

FOREIGN PATENT DOCUMENTS

| | | |
|---|---|---|
| JP | 2005-244710 A | 9/2005 |
| JP | 2005-250778 A | 9/2005 |
| JP | 2010-045613 A | 2/2010 |
| JP | 2012-079089 A | 4/2012 |
| JP | 2014-016666 A | 1/2014 |
| JP | 2016-071588 A | 5/2016 |

OTHER PUBLICATIONS

Unsupervised Segmentation of Medical Images using DCT Coefficients (Year: 2004).*
Improved Block-based Image Segmentation (Year: 1999).*
A Robust Automatic Clustering Scheme for Image Segmentation Using Wavelets (Year: 1996).*
CytoSpectre: a tool for spectral analysis of oriented structures on cellular and subcellular levels (Year: 2015).*
International Search Report dated Feb. 5, 2019 in corresponding PCT International Application No. PCT/JP2018/043983.
Written Opinion dated Feb. 5, 2019 in corresponding PCT International Application No. PCT/JP2018/043983.
Extended European Search Report dated Nov. 12, 2021 for counterpart European Application No. 18911181.8.
Kim, Seule Ki et al.: "*I'mCell*: A touch pad tool for annotating cell images" Proceedings of the 1st Biomedical Slgna Analysis Conference, Mar. 25, 2014, pp. 1-3, XP055853411, Retneved from the Internet: URL:http://www.cs.bu.edu/faculty/betke/papers/Kim-etal-ImCel1-BSA-2014.pdf [retrieved on Oct. 21, 2021].

* cited by examiner

FIG. 7B

IMAGE PROCESSING METHOD AND COMPUTER-READABLE RECORDING MEDIUM HAVING RECORDED THEREON IMAGE PROCESSING PROGRAM

CROSS-REFERENCE TO RELATED APPLICATIONS

The present application is a 35 U.S.C. §§ 371 national phase conversion of International Application No. PCT/JP2018/043983, filed Nov. 29, 2018, which claims priority to Japanese Patent Application No. 2018-050932, filed Mar. 19, 2018, the contents of both of which are incorporated herein by reference. The PCT International Application was published in the Japanese language.

TECHNICAL FIELD

This invention relates to an image processing technique for dividing a cell area and another area from an image captured in a culture environment and including a cell image and a background image thereof.

BACKGROUND ART

In an image captured to include a cell image in a culture environment, a cell area, which is a primary imaging object, and an area equivalent to a background image of the cell image may be distinguished in the image. For example, to obtain the size of the cell, a boundary between the cell image and the background image needs to be defined. Conventionally, a cell area has been specified, for example, by dying the cell with a drug or adding a fluorescence reagent. However, it is required in some cases to specify a cell area without using a process of modifying the cell as an imaging object, such as for the purpose of observing a change of the cell with time.

A cell in a culture medium is close to transparent and has a refractive index not much different from that of water. Thus, in a captured image, a boundary between a cell image and a background image is often unclear. To address this problem, the applicant of this application has, thus far, proposed a bright field imaging technique capable of obtaining an image in which the contour of a cell image particularly clearly appears (for example, see patent literature 1). An image processing technique such as a binarization processing utilizing a luminance difference between a cell image and a background image or edge detection for extracting a cell contour can be utilized to distinguish the cell image and the background image in an image.

CITATION LIST

Patent Literature

[PTL 1] JP 2016-071588A

SUMMARY OF INVENTION

Technical Problem

In the case of observing cells in a culture environment with time, what is included in an image captured in an initial stage of culture is images of the cells and a culture medium, which becomes a substantially uniform background. Thus, the cell images and the background image are relatively easily discriminated. However, as the culture progresses, wastes discharged from the cells, the debris of dead cells and the like (hereinafter, collectively referred to as "debris") appear around the cells as imaging objects and are included in an image. Thus, it is difficult to properly discriminate the cell images and debris images by a simple processing such as the binarization processing or the edge detection.

Solution to Problem

This invention was developed in view of the above problem and an object thereof is to provide a technique capable of properly segmenting a cell area and another area from an image including a cell image and a background image.

To achieve the above object, one aspect of an image processing method according to this invention includes obtaining an original image including a cultured cell image with a background image, dividing the original image into blocks each composed of a predetermined number of pixels and obtaining a spatial frequency component of an image in each block for each block, setting a total of intensities of low frequency components having a frequency equal to or lower than a predetermined frequency as a first feature amount, setting a total of intensities of high frequency components having a higher frequency than the low frequency component as a second feature amount and classifying each block as the one belonging to a cell cluster corresponding to the cell or the one belonging to other than the cell cluster in a two-dimensional feature amount space composed of the first feature amounts and the second feature amounts, and segmenting the original image into an area occupied by the blocks classified as the cell cluster and another area.

In the invention thus configured, an image is segmented based on a distribution of local spatial frequency components in the image. Specifically, the image is divided into blocks and the spatial frequency component is obtained for each block. Out of the spatial frequency components, the low frequency component represents a moderate luminance change in the block and the high frequency component represents a state of a finer luminance change. Note that, out of the low frequency components, a direct-current component particularly represents an average luminance of the entire block. Thus, in the case of expressing the block by the intensity of each spatial frequency component in this way, the low frequency component reflects the brightness of this block and the high frequency component reflects a texture in the block.

When these are handled as feature amounts of the block, positions occupied in the two-dimensional feature amount space are considered. Then a significant difference appears in a distribution of the feature amounts between the blocks falling under the cell area and blocks falling under the background, and these blocks form mutually independent clusters. If a debris image is included in the image, the blocks falling under the debris image form a cluster different from the clusters of both the cell and the background. Utilizing this, the positions in the original image occupied by the blocks belonging to the cell cluster in the feature amount space can be regarded as the cell area. By doing so, the cell area can be precisely extracted from the original image without being affected by the debris.

The image processing method according to the invention can make a computer an execution subject. In this sense, the invention can be realized as a computer program for causing the computer to perform the above processing. Further, the invention can be realized as a recording medium recording this computer program.

Advantageous Effects of Invention

As described above, according to the image processing method of the invention, whether or not a block is equivalent to a cell is evaluated based on features of a spatial frequency component of an image in the block for each of the blocks obtained by dividing an original image. Thus, a cell area and another area can be properly separated from an image including a cell image and a background image.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF EMBODIMENTS

Hereinafter, one embodiment of an image processing method according to the invention is described. An image processing in this embodiment is an area segmentation processing for extracting a cell area from an image captured by imaging a cell or an aggregate of cells cultured in a culture medium. This image processing is performed for an unprocessed original image captured by an imaging device having an imaging function of imaging a specimen including a cell. The imaging device can perform this image processing as one of post-processings for image data after imaging. Further, a computer device having received image data from the imaging device or an appropriate storage may perform this image processing.

Herein, an aspect in which a general-purpose computer device performs the image processing of the present embodiment on original image data generated by imaging which is already performed will be exemplarily described. The configuration of the imaging apparatus is not particularly limited only if the imaging apparatus has a function of imaging a sample including cultured cells together with a culture medium and outputting the captured image as digital image data. Further, it is preferable that the image should be a bright field image. Furthermore, the computer device having a general hardware configuration, which is commercialized as, for example, a personal computer, can be used. Hereinafter, detailed description on the hardware will be omitted.

Figure 1:
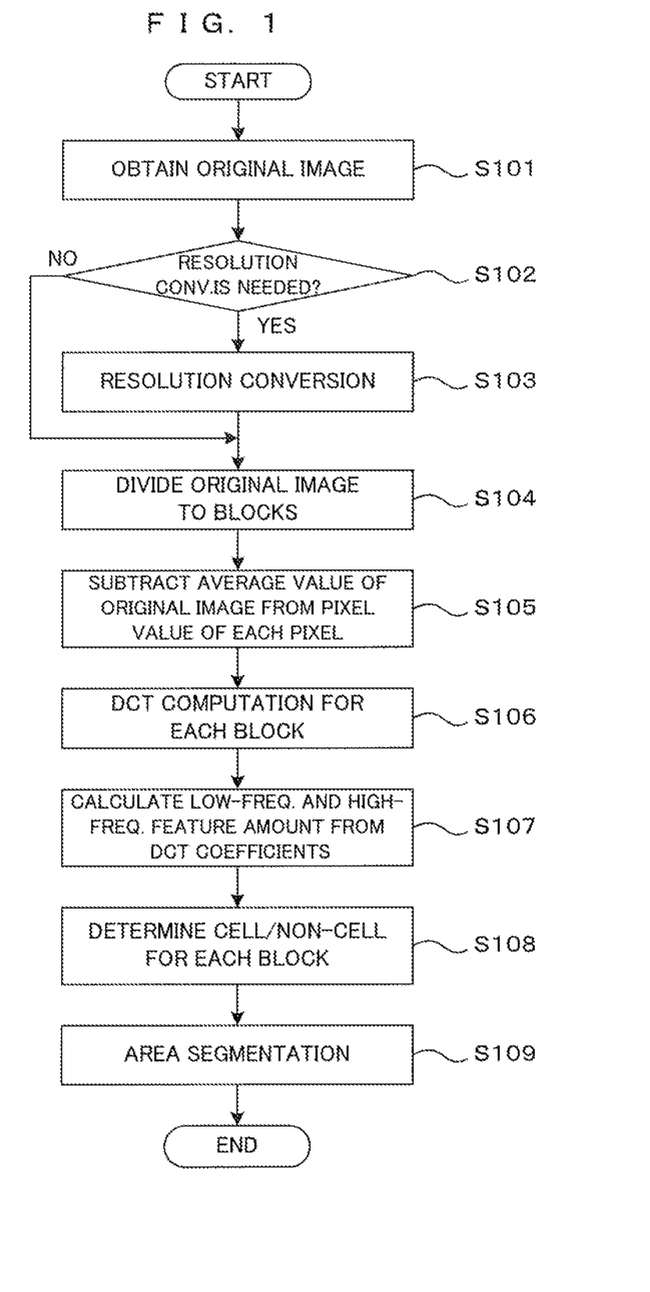
FIG. 1 is a flow chart showing an area segmentation processing of this embodiment.

FIG. 1 is a flow chart showing an area segmentation processing of this embodiment. First, with reference to FIG. 1, the area segmentation processing in this embodiment is summarized. Thereafter, specific contents of the processing are described in detail. The computer device obtains an original image (Step S101). The original image is an image obtained by bright-field imaging a specimen including a cell cultured in a culture medium under appropriate imaging conditions by an appropriate imaging device, and assumed to include at least one entire cell image. Thus, the original image can include images of at least one cell and a debris other than the cell around the cell, a background and the like.

It is judged for the obtained original image whether or not a resolution conversion is necessary (Step S102). The resolution conversion is a processing of converting a pixel size of the original image at the time of imaging to a pixel size suitable for the area segmentation processing. The resolution conversion is performed (Step S103) if it is judged to be necessary.

In the following description, both the image before the resolution conversion and the image after the conversion are referred to as the "original images". Further, a "pixel" merely mentioned without particular specification indicates a pixel of the original image subjected to processings in and after Step S104. The pixel after the conversion is the "pixel" mentioned here if the resolution conversion is performed and the pixel at the time of imaging is the "pixel" mentioned here if the resolution conversion is not performed. Note that, when particular distinction is necessary, the pixel before the conversion (i.e. at the time of imaging) may be referred to as an "original pixel". Specifically, the "original pixel" means the pixel at the time of imaging regardless of whether or not the resolution conversion is performed.

The original image is divided into a plurality of blocks (Step S104). In this embodiment, a square constituted by 4 pixels by 4 pixels in the original image is set as one block. When the resolution conversion was performed, the pixels mentioned here are the pixels after the conversion as described above. If the number of the pixels of one line is not exactly divisible by the number 4 of the pixels on one side of one block, the pixels not included in the processing may be present in an end part of the original image. Further, the end part of the original image may be cut off in advance so that fractions are not present.

Subsequently, an average pixel value in the entire original image is subtracted as an offset value from a pixel value of each pixel (Step S105). This processing is for level shifting for the convenience of later computation. If the pixel value is expressed, for example, as 8-bit data, each pixel can have a value in 256 levels from 0 to 255. By subtracting the average pixel value, some pixels have a negative value as the pixel value.

A spatial frequency component is obtained for each of the blocks divided in this way. To this end, two-dimensional discrete cosine transport (hereinafter, abbreviated as "DCT") computation is utilized in this embodiment (Step S106). An image content of each block is decomposed into a two-dimensional spatial frequency component by the two-dimensional DCT computation, for example, similarly to a processing in the JPEG (Joint Photographic Exerts Group) image compression technique.

The image content of the block can be reproduced by synthesizing respective frequency components. An intensity of each frequency component differs depending on the image content. As known in the JPEG image compression theory, the intensity of each frequency component is obtained as a DCT coefficient obtained by the DCT computation.

Out of the spatial frequency component, a low frequency component represents a moderate brightness change in the image within the block. Particularly, out of this low frequency component, a direct-current component is equivalent to a brightness average value of this block. On the other hand, a high frequency component represents a finer brightness change and has information on the texture of the image in the block. Accordingly, a total value of the frequency components lower than a certain spatial frequency is set as a feature amount (first feature amount) corresponding to the brightness of this block based on the obtained DCT coefficient. Further, a total value of the frequency components having a frequency higher than the certain spatial frequency is set as a feature amount (second feature amount) corresponding to the texture of the block. These two types of the feature amounts are respectively calculated (Step S107).

By doing so, one block can be represented by the low frequency feature amount indicating the brightness and the high frequency feature amount indicating the texture. As an example, the spatial frequency component of the image can be divided into a direct-current component and an alternating-current component. In this case, the direct-current component can be set as the feature amount (first feature amount) indicating the brightness of the block and the alternating-current component can be set as the feature amount (second feature amount) indicating the texture in the block.

In this way, the features of the image of each block are represented by the low frequency feature amount indicating the brightness and the high frequency feature amount indicating the texture. Whether the block corresponds to the cell or a non-cell other than the cell is determined based on which of the feature of an in-cell area and the feature of the other area the block represented by these feature amounts strongly exhibits (Step S108). Whether the block is equivalent to the cell or the non-cell is determined for each block and the original image is divided into a cell area and a non-cell area based on a result of the determination (Step S109). The above is a summary of the area segmentation processing of this embodiment.

Figure 2:
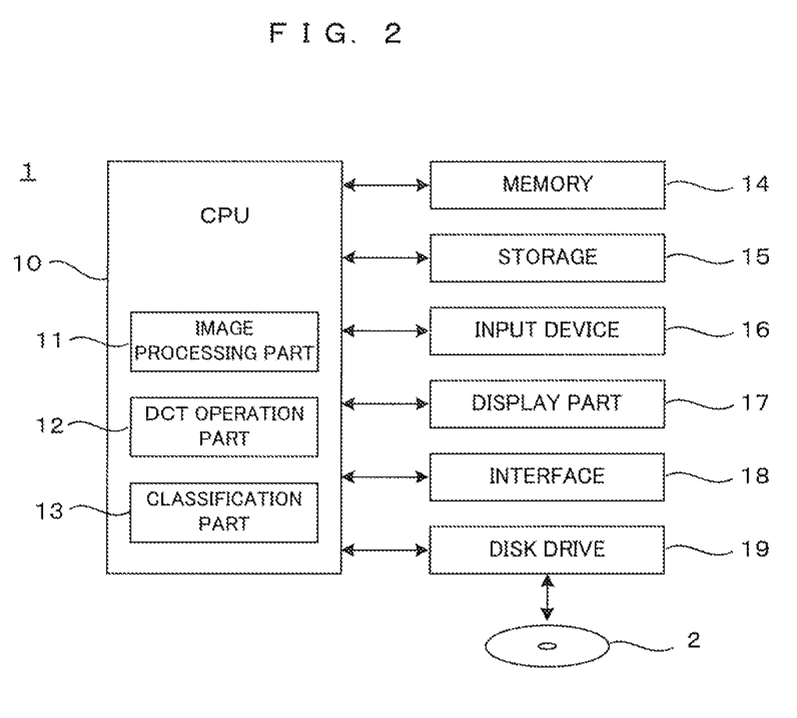
FIG. 2 is a diagram showing an exemplary configuration of a computer device which performs the area dividing process of the present embodiment.

FIG. 2 is a diagram showing an exemplary configuration of a computer device which performs the area dividing process of the present embodiment. The computer device 1 has, for example, a general configuration as a personal computer, and includes a CPU (Central Processing Unit) 10, a memory 14, a storage 15, an input device 16, a display part 17, an interface 18, a disk drive 19, and the like.

The CPU 10 executes a control program prepared in advance. Thereby function blocks for performing the area segmentation process, i.e., an image processing part 11, a DCT operation part 12, a classification part 13, and the like are implemented by software. Note that these function blocks may be configured by dedicated hardware. The memory 14 temporarily stores therein various data generated during the operation performed by the CPU 10. The storage 15 stores therein the control program to be executed by the CPU 10 and image data of the original image, processed image data, and the like in the long term.

The input device 16 serves to receive an instruction input from an operator, and includes a mouse, a keyboard, or the like. Further, the display part 17 is, for example, a liquid crystal display having a function of displaying an image, and displays thereon the original image, the processed image, and various information such as a message to the operator and the like. Note that a touch panel in which the input device and the display part are unified may be provided.

The interface 18 exchanges various data with an external device via a telecommunications line. The disk drive 19 takes in an external recording disk 2 which records therein various data such as the image data, the control program, and the like. The image data, the control program, or the like stored in the recording disk 2 is read by the disk drive 19 and stored into the storage 15. The disk drive 19 may have a function of writing data generated inside the computer device 1 into the recording disk 2.

The control program for causing the computer device 1 to perform the area segmentation processing of this embodiment can be read by the disk drive 19 accessing to the recording disk 2 having the control program recorded thereon. Further, the control program may be given from an external apparatus via the interface 18. The same also applies to the original image data.

The image processing unit 11 performs image processings such as the resolution conversion of the original image, block division and final area segmentation of the image. Further, the DCT computing unit 12 obtains the spatial frequency component for each block by performing the DCT computation described above. The classifying unit 13 classifies each block as one corresponding to the cell or one not corresponding to the cell based on the feature amounts obtained for each block.

Figure 3A:
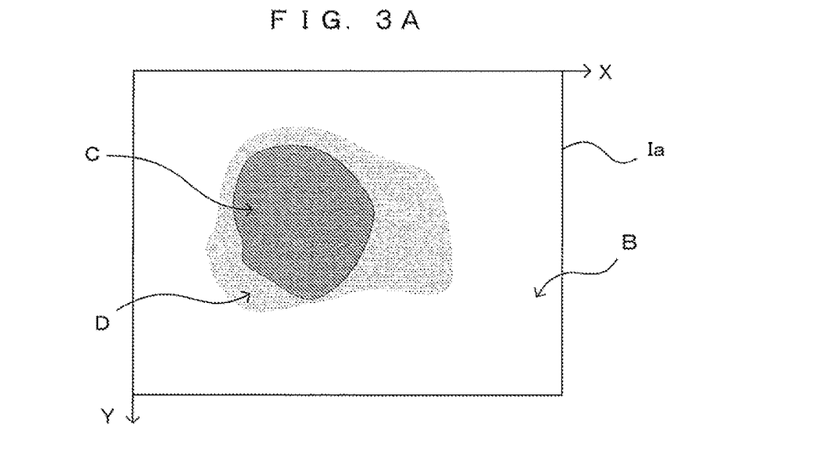
FIG. 3A is a first diagram showing an example of an original image.
Figure 3B:
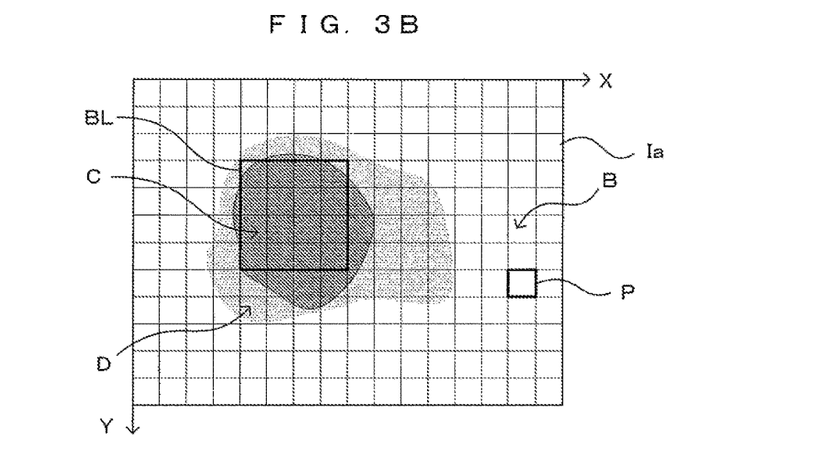
FIG. 3B is a second diagram showing an example of an original image.
Figure 3C:
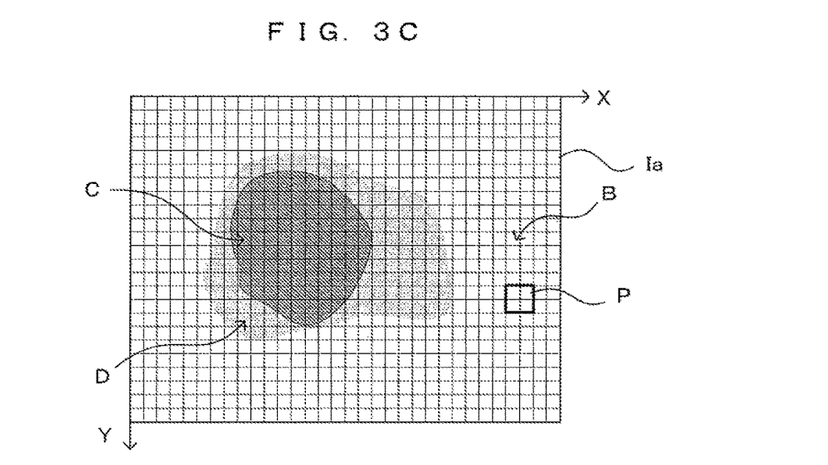
FIG. 3C is a third diagram showing an example of an original image.

FIGS. 3A through 3C are drawings showing an example of an original image. As shown in FIG. 3A, it is assumed that an original image Ia obtained in Step S101 includes, as image objects, a cell image C, a debris image D distributed around the cell and a background image B corresponding to a culture medium. In the figures, it is defined that a horizontal-direction coordinate of the image is an X coordinate and a vertical-direction coordinate is a Y coordinate. The shapes and densities of these image objects are merely examples and actually obtained images can have various shapes and densities. Note that the debris is not necessarily always present and the original image may be composed of the cell image C and the background image B. Further, the image may be possibly occupied by the cell image C and the debris image D and no background image corresponding to the culture medium may not be included. Further, the background image B does not necessarily constantly have the same brightness due to the amount of the culture medium, illumination conditions at the time of imaging and the like.

From these, the arrangement, densities and the like relationships of the cell area and the other areas in the image should be thought to be different in each original image. The image processings described here are established regardless of these relationships. A basic way of thinking of the area segmentation processing in this embodiment is to divide the original image Ia into small blocks and determine which of the image feature of the cell image C or the other feature the block strongly exhibits based on the spatial frequency component of each block.

In this area segmentation processing, the original image Ia is divided into square blocks having a predetermined size. In FIG. 3B, reference sign P denotes one pixel. As shown in FIG. 3B, one block BL is a square area composed of a total of 16 pixels P, 4 pixels in each of X and Y directions. The size of the block BL is desirably set according to the size of the cell image C as an extraction object in the image.

If the block size is too small, one block includes only a very small part of the cell. Thus, the block cannot sufficiently reflect characteristic properties of the cell in the image on the processing, leading to an accuracy reduction of the area segmentation. Further, if the block size is too large, the feature of the cell and the features of the other objects are mixed in one block, which also causes an accuracy reduction. According to the knowledge of the inventors of this application, the size of the block BL is preferably so selected that substantially one block enters the cell image C as the extraction object in the image.

If the cell image C is, for example, a somatic cell of a human, a diameter thereof is substantially about 10 μm to 20 μm. Thus, the size of the block BL is preferably such that a length of one side converted into a specimen size is about equal or slightly smaller than this diameter. From this, the size of one pixel P is preferably such that one side is 2.5 μm to 5 μm or slightly smaller.

If a resolution in imaging is, for example, 6400 dpi (dots per inch), the pixel size is about 4 μm. Further, if the resolution is 16000 dpi, the pixel size is about 1.6 μm. From this, a value from 6400 dpi to 16000 dpi is preferable as a resolution necessary to obtain the size of the pixel P described above. However, these are values suitable to perform the area segmentation processing of this embodiment. It is fundamental to perform imaging at as high a resolution as possible at the time of imaging without limitation to this.

For example, when an original image can be captured at a resolution of 32000 dpi (pixel size of 0.8 μm), it is not necessary to reduce the resolution at the time of imaging for the convenience of the area segmentation processing. In this case, as shown in FIG. 3C, four pixels in the original image Ia at the time of imaging is regarded as one pixel P in a pseudo manner and an average pixel value of those pixels is set as a pixel value of this pixel P. By doing so, the pixel size (1.6 μm) suitable for the area segmentation processing can be obtained without reducing the resolution at the time of imaging. In this embodiment, such a processing is referred to as a "resolution conversion".

Whether or not the resolution conversion is necessary is determined by a relationship of the pixel size at the time of imaging and the size of the cell image C as a processing object. If the relationship of those is known in advance, whether or not the resolution conversion is necessary can be judged from that known relationship. Further, whether or not to perform the resolution conversion may be determined based on an instruction input from a user. If it is judged to be necessary, the resolution conversion is performed (Step S103).

When the resolution conversion is performed, a square constituted by 4 pixels by 4 pixels in the image after the conversion is set as one block BL. Unless the resolution conversion is performed, a square constituted by 4 pixels by 4 pixels in the image at the time of capturing the original image Ia is set as one block BL. If the number of the pixels of one line is exactly divisible by the number 4 of the pixels of one side of one block in at least either one of X and Y directions, the pixels not included in the processing may be present in an end part of the original image. Further, the end part of the original image may be cut off in advance so that such fractions are not present.

Subsequently, the average pixel value in the entire original image Ia is subtracted as the offset value from the pixel value of each pixel (Step S105). If the pixel value is expressed, for example, as 8-bit data, each pixel can have a value in 256 levels from 0 to 255. By subtracting the average pixel value, some pixels have a negative value as the pixel value. According to the knowledge of the inventors of this application, since a difference between a maximum pixel value and a minimum pixel value is relatively small in a cell image, the positive and negative balance of each pixel value is improved by subtracting the average pixel value of the entire image from each pixel. When p(X, Y) denotes the pixel value of each pixel P and $p_{av}$ denotes the average pixel value, a pixel value g(X, Y) of the image P after subtraction is expressed by the following (Equation 1).

$$g(X,Y)=p(X,Y)-p_{av} \quad \text{(Equation 1)}$$

The DCT computation is performed for each of the thus divided blocks (Step S106). An image content of each block is decomposed into a two-dimensional spatial frequency component in each of the X and Y directions by the DCT computation. The DCT computation processing is widely known as also utilized in the JPEG image compression processing. Thus, items to which the same way of thinking as the JPEG image compression processing can be applied are not described below.

Figure 4:
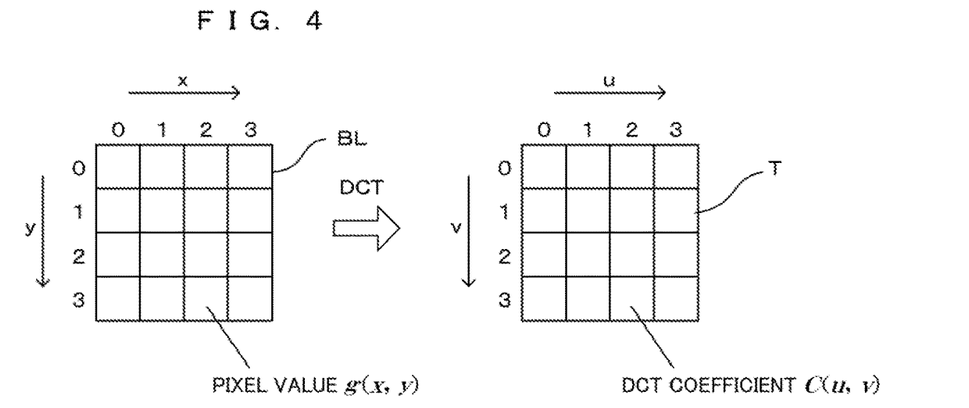
FIG. 4 is a diagram showing a concept of the DCT computation.

FIG. 4 is diagrams showing a concept of the DCT computation. The left diagram shows one block BL, which is a part of the original image and composed of (4×4) pixels. Small letters are used to express the position of each pixel in the block in such a manner as to be distinguished from a coordinate position in the original image, a horizontal-direction coordinate is an x coordinate, and a vertical-direction coordinate is a y coordinate. The DCT computation can be considered as a computation of obtaining a 4×4 DCT coefficient table T shown in the right diagram of FIG. 4 from the pixel value g(x, y) of each pixel in the block BL.

A column position u (u=0, 1, 2, 3) in the DCT coefficient table T represents a spatial frequency component in an x direction. Specifically, u=0 represents a direct-current component, u=1 represents a fundamental frequency component and u=2, u=3 respectively represent components having frequencies twice and three times as high as a fundamental frequency. Similarly, a row position v (v=0, 1, 2, 3) represents a space frequency component in a y direction. Further, v=0 represents a direct-current component, v=1 represents a fundamental frequency component and v=2, v=3 respectively represent components having frequencies twice and three times as high as a fundamental frequency.

A DCT coefficient C(u, v) indicating an intensity of each frequency component is expressed by the following (Equation 2).

$$C(u, v) = \frac{2}{N} p_u p_v \sum_{x=0}^{N-1} \sum_{y=0}^{N-1} g(x, y) \cos\frac{(2x+1)u\pi}{2N} \cos\frac{(2y+1)v\pi}{2N} \quad \text{(Equation 2)}$$

where $$p_u = \begin{cases} 1/\sqrt{2}, & u = 0 \\ 1, & u \neq 0 \end{cases},$$

$$p_v = \begin{cases} 1/\sqrt{2}, & v = 0 \\ 1, & v \neq 0 \end{cases}$$

Here, a constant N denotes a block size. In the JPEG system, N=8, i.e. (8×8) pixels constitute one block. However, in this embodiment, N=4 since (4×4) pixels constitute one block as described above. According to the knowledge of the inventors of this application, a better result is obtained in this processing method utilizing the DCT coefficient as a feature amount without aiming to compress/decompress an image if the block size is (4×4) pixels. Further, this can also reduce an amount of computation and is suitable for speed-up.

Out of the DCT coefficients C(u, v) constituting the DCT coefficient table T, a coefficient indicating a component having a frequency equal to or lower than a predetermined frequency, e.g. a coefficient C(0, 0) of a direct-current component, is set as a low-frequency feature amount. Further, a total of the other coefficients is set as a high-frequency feature amount. Note that the DCT coefficient can have either a positive or negative value. To avoid the offset of those values at the time of totaling, the total of the DCT coefficients may be obtained as the sum of absolute values of the respective DCT coefficients.

Whether each block is equivalent to the "cell image" or the "non-cell image" is determined based on the low-frequency feature amount and the high-frequency feature amount obtained in this way (Step S108). This determination is made based on the position of the block in a two-dimensional feature amount space constituted by the low-frequency feature amounts and the high-frequency feature amounts. To make the determination, a determination criteria, specifically a range occupied by features of the "cell image" in the two-dimensional feature amount space, needs to be specified in advance.

It is assumed that the type of cells to be imaged, the type and amount of culture media and imaging conditions (imaging magnification, illumination intensity, etc.) are fixed among a plurality of imaging operations. In this case, a range occupied by a cell cluster in a two-dimensional feature amount space can be specified in advance by collecting a multitude of images of typical cells imaged under the same conditions as case examples and using an appropriate machine learning algorithm. By doing so, whether or not a block corresponds to a cell or a non-cell can be determined based on whether or not feature amounts of the block selected from an unknown original image belongs to the cell cluster.

However, generally, imaging conditions and the like differ for each original image. Thus, to make a more accurate determination, it is convenient if the determination criteria can be established from information read from an original image as a processing object. An example of such a method is described below.

Figure 5:
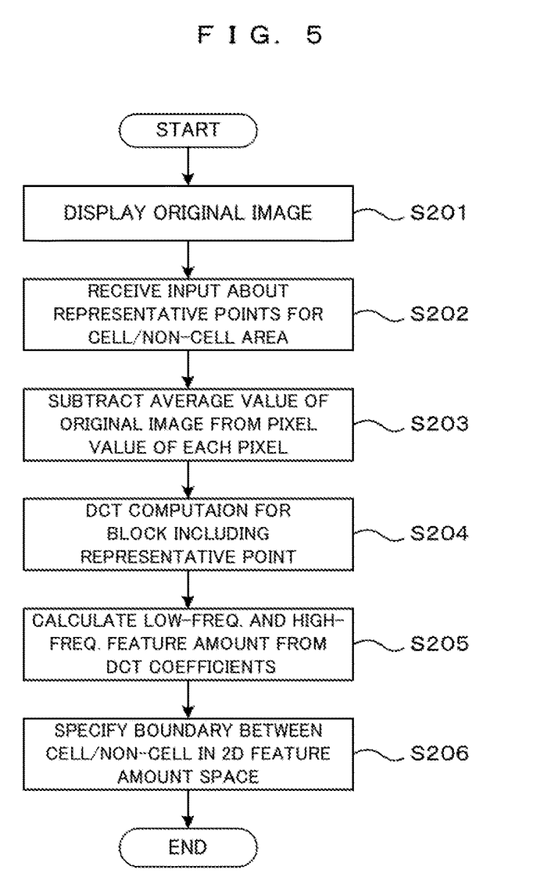
FIG. 5 is a flow chart showing a processing of establishing the determination criteria.
Figure 6A:
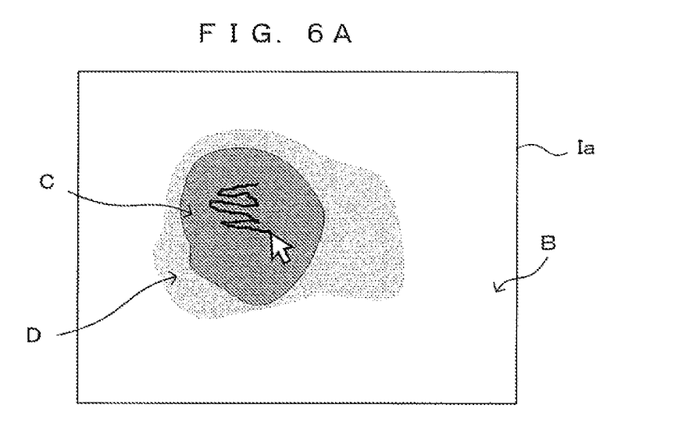
FIG. 6A is a first diagram illustrating an instruction input mode in a processing process.
Figure 6B:
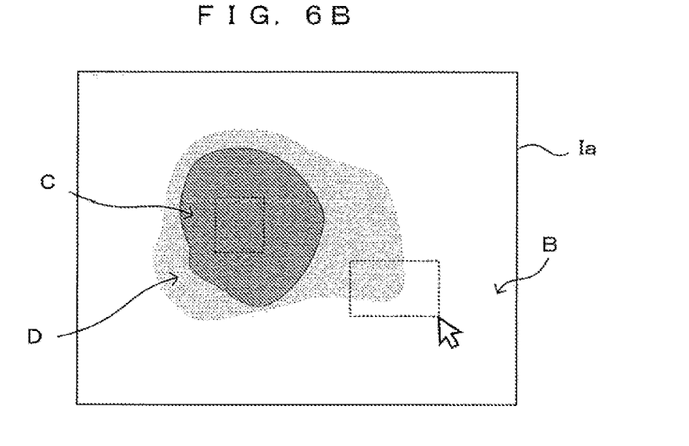
FIG. 6B is a second diagram illustrating an instruction input mode in a processing process.
Figure 6C:
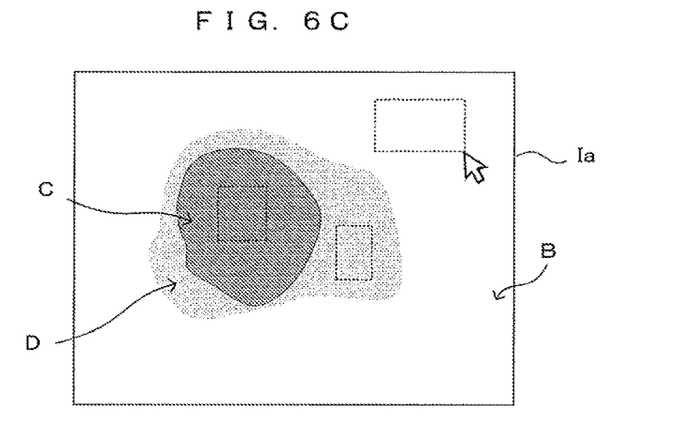
FIG. 6C is a third diagram illustrating an instruction input mode in a processing process.

FIG. 5 is a flow chart showing a processing of establishing the determination criteria. Further, FIGS. 6A through 6C are diagrams illustrating instruction input modes in a processing process. This processing is to receive an instruction from an operator for a typical example having strong features of a cell image and a non-cell image, out of an obtained original image Ia, and specify a boundary between the cell image and the non-cell image in a two-dimensional feature amount space from the received information. This processing can be performed at an arbitrary timing until the classification of the blocks (Step S108) is started after the computer device 1 obtained the original image Ia (Step S101). The processing is realized by the CPU 10 executing the control program stored in the storage 15.

At first, the obtained original image Ia is displayed on the display unit 17 and presented to the operator (Step S201).

Then, an instruction input from the operator designating a representative point belonging to a cell area and a representative point corresponding to a non-cell area in the displayed original image Ia is received (Step S202). Note that if the cell area and the non-cell area are clearly different in appearance, only the representative point belonging to the cell area may be designated.

To improve accuracy, it is desirable to designate a plurality of representative points. Accordingly, as shown in FIG. 6A, for example, the operator is caused to continuously move a pointer in an area of the cell image C through a mouse operation or touch pen input. By doing so, a plurality of points on that trace can be obtained and collected as representative points of the cell image C. A white arrow in FIG. 6A indicates the pointer moving on a screen in association with the operation of a mouse or the like by a user.

Further, as indicated by dotted lines in FIG. 6B, a rectangular area belonging to the cell image C, a rectangular area outside the cell image and the like may be designated as two-dimensional areas. If a debris image D and a background image B are present in the image, it is desirable to include both an area of the debris image D and an area of the background image B in designating the area outside the cell. By doing so, representative points extracted from the area outside the cell include both those having features of the debris image D and those having features of the background image B. Thus, information on the non-cell can be more strongly reflected in determining the boundary between the cell area and the non-cell area in the feature amount space.

Further, as indicated by dotted lines in FIG. 6C, an area of the cell image C, an area of the debris image D and an area of the background image B may be respectively individually designated. Representative points selected from the thus designated ranges respectively form a cell cluster, a debris cluster and a background cluster in the feature amount space. Thus, not only the cell image and the non-cell image can be segmented, but also the area segmentation can be performed, for example, between the background image and the debris image.

When several representative points are designated in this way, an average pixel value in the entire original image Ia is subtracted from the pixel value of each pixel similarly to the area segmentation processing described above (Step S203). The DCT computation is performed (Step S204) and the low-frequency feature amount and the high-frequency feature amount are calculated from the DCT coefficient (Step S205) for each virtual block of the (4×4) pixel size including the representative point. In this way, a distribution in the two-dimensional feature amount space when the blocks including the representative points are typical examples becomes clear. From that result, the boundary between a region of the "cell image" and a region of the "non-cell image" in the two-dimensional feature amount space can be specified (Step S206).

Various methods known as clustering techniques in a feature amount space based on values of feature amounts can be appropriately selected and used to specify a boundary. However, since the number of the typical examples is not many, an advantage of applying a complicated learning algorithm is little. Thus, it is also possible to use a simpler method as described below.

Figure 7A:
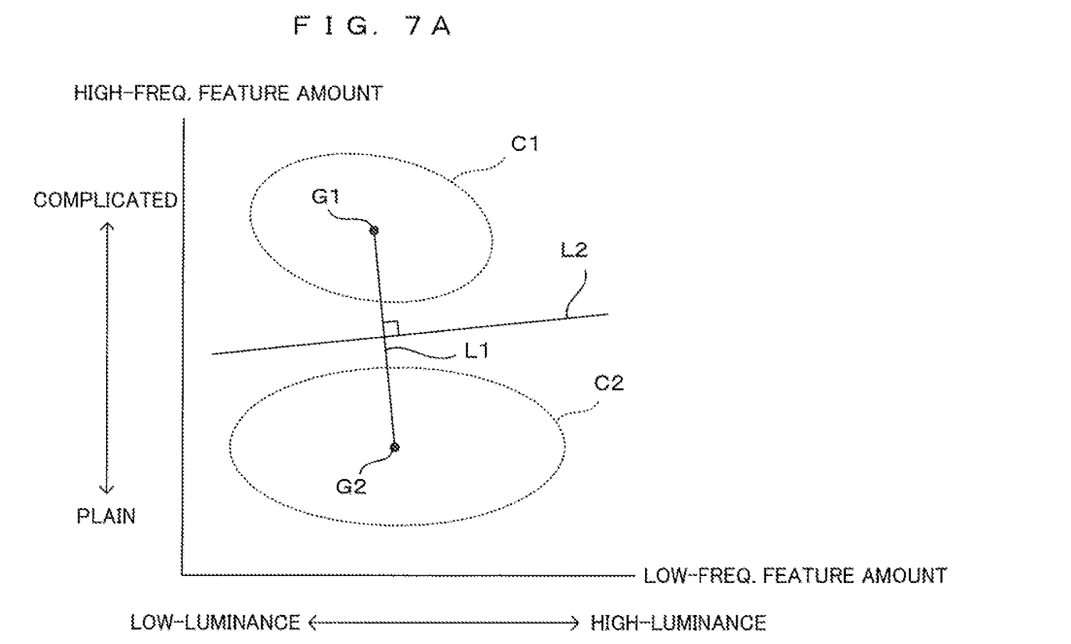
FIG. 7A is a first diagram showing an example of boundary specification method in a feature amount space.
Figure 7B:
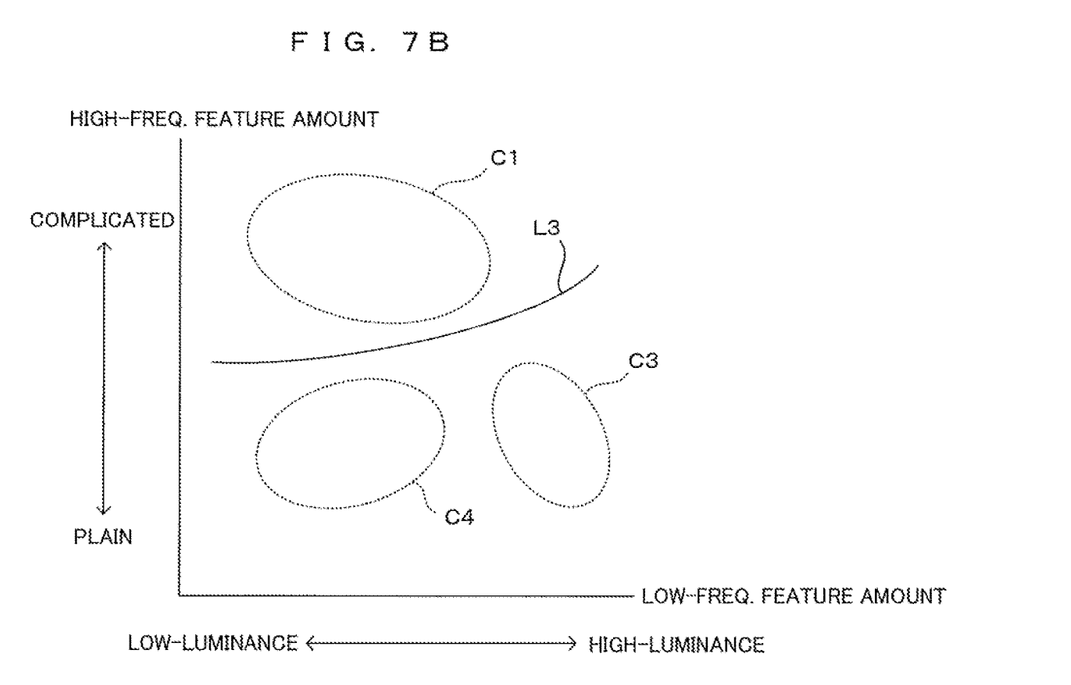
FIG. 7B is a second diagram showing an example of boundary specification method in a feature amount space.

FIGS. 7A and 7B are graphs showing examples of boundary specification methods in a feature amount space. When a cell area and a non-cell area are designated by the user using the method shown in FIG. 6A or 6B, the low-frequency feature amount and the high-frequency feature amount are obtained for each of several blocks including the representative points in those areas. If the respective blocks are plotted in the two-dimensional feature amount space, it is thought that two clusters, i.e. a cluster (cell cluster) C1 corresponding to the cell image C and a cluster (non-cell cluster) C2 corresponding to the non-cell, i.e. the background image B and the debris image D, are formed due to differences of image features of the cell image and the non-cell image as shown in FIG. 7A.

Center-of-gravity points G1, G2 of these clusters C1, C2 can be respectively specified, and a perpendicular bisector L2 to a line segment L1 connecting these center-of-gravity points G1, G2 can be set as a boundary dividing the cell image and the non-cell image in the feature amount space. In determination for each block in the area segmentation processing (Step S108), if a set of the low-frequency feature amount and the high-frequency feature amount representing the image features of each block is expressed as a point closer to the cell cluster C1 with respect to the boundary line L2, this block is determined to correspond to the cell image C. On the other hand, if this set of the feature amounts is expressed as a point closer to the non-cell cluster C2, this block is determined to correspond to the non-cell image.

In a case where an area corresponding to the cell image C, an area corresponding to the background image B and an area corresponding to the debris image D are respectively designated as shown in FIG. 6C, a cluster C1 corresponding to the cell image C, a cluster C3 corresponding to the background image B and a cluster C4 corresponding to the debris image D are formed in the feature amount space as shown in FIG. 7B. By specifying an appropriate straight line or curve L3 capable of clearly separating the cell cluster C1 from the other clusters, this curve L3 can be set as a boundary dividing the cell image and the non-cell image.

As described above, in the area segmentation processing of this embodiment, an original image including a cell image is divided into a plurality of small blocks and a spatial frequency component of each block is obtained. Then, the block is classified according to a position occupied in a two-dimensional feature amount space by a set of a low-frequency feature amount (first feature amount) based on an intensity of a low frequency component and a high-frequency feature amount (second feature amount) based on an intensity of a high frequency component. More specifically, whether an image of the block corresponds to the cell or the non-cell other than the cell is determined based on whether or not this block belongs to the cell cluster in the two-dimensional feature amount space.

The low-frequency feature amount represents the brightness and a relatively simple structure of the block and the high-frequency feature amount represents a fine texture in the block. By comprehensively evaluating the brightness and the texture in this way, the cell area and the non-cell area in the image can be distinguished with better accuracy than in the area segmentation merely by a binarization processing or a contour extraction processing.

Note that the invention is not limited to the embodiment described above and various changes other than the aforementioned ones can be made without departing from the gist of the invention. For example, in the area segmentation of the original image (Step S109) in the above embodiment, the original image is segmented into the cell image and the non-cell image block by block. However, the block boundary is automatically established and does not necessarily coincide with the boundary between the cell image and the non-cell image in the original image. In view of this, the original image may be segmented, for example, in combination with the known contour extraction processing. Specifically, the position of the boundary between the cell area and the non-cell area specified block by block as described above may be corrected based on a result of the contour extraction processing.

Further, the processing of specifying the boundary of the cell cluster in the two-dimensional feature amount space in the above embodiment is merely illustrative. Besides this, various clustering methods can be applied. Further, the method for collecting the typical examples of the cell image and the non-cell image is also not limited to the above method.

Further, in the above embodiment, the direct-current component C(0, 0) of the DCT coefficient is used for the low-frequency feature amount and the sum of the absolute values of the other DCT coefficients is used for the high-frequency feature amount. That is, the DCT coefficient of the direct-current component is set as the low-frequency feature amount and the sum of the absolute values of the DCT coefficients of the alternating-current components is set as the high-frequency feature amount. However, the frequency for distinguishing the low-frequency feature amount and the high-frequency feature amount is not limited to this and may be a relatively low alternating-current frequency. Further, if there is a method for appropriately obtaining the spatial frequency component besides the DCT computation, such a method may be utilized.

Further, although the area segmentation processing is performed by the general-purpose computer device 1 in the above embodiment, this processing function may be, for example, incorporated into the imaging device as described above. Further, it is also possible to expand functions by additionally mounting a program for performing the area segmentation processing of this embodiment in an existing imaging device.

Further, although specific numerical values of the pixel size and the block size are illustrated in the above description, the area segmentation processing of this embodiment can be performed under conditions outside these numerical value ranges.

As the specific embodiment has been illustrated and described above, in the present invention, an intensity of a direct-current component out of spatial frequency components can be set as the first feature amount and a total of intensities of alternating-current components can be set as the second feature amount. Out of the spatial frequency components, the direct-current component represents an average brightness of a block and the alternating-current components represent a brightness change mode, i.e. a texture, in the block. Thus, the image is segmented based on the feature amounts indicating the brightness and the texture in the block, and area segmentation having a higher accuracy than a mere binarization processing or contour extraction processing is possible.

Further, the two-dimensional discrete cosine transform can be performed for each block based on the pixel values of the pixels included in this block, and the intensity of each frequency component can be obtained as a discrete cosine transform coefficient of this frequency component. Such a processing is also utilized in the JPEG image compression processing and a computation algorithm is already established. Thus, this can be also applied to the invention.

In this case, the two-dimensional discrete cosine transform can be performed based on values obtained by subtracting an average pixel value of the entire original image from the pixel values of the respective pixels. Since a distribution range of pixel values is small in an image obtained by imaging a cell close to transparent, a level shift for discrete cosine transform computation is preferably performed using the average pixel value of the entire original image.

Further, a total of intensities of a plurality of frequency components can be obtained as the sum of absolute values of discrete cosine transform coefficients of the respective frequency components. Since the discrete cosine transform coefficients can have either a positive or negative value, the respective frequency components may be offset and a good result may not be obtained by simple totaling. By taking the sum of the absolute values, this problem can be solved.

Further, each block can be a square, the size of one side of which is equivalent to 4 pixels. The block size is 8 pixels in the JPEG image compression. However, according to the knowledge of the inventors of this application, a better result is obtained if the block size is set at 4 pixels in the invention not aiming to compress/decompress an image.

Further, it is possible to provide a step of converting a pixel size of an original image from an original pixel size when this original image was obtained to a pixel size for block division different from the original pixel size prior to the division of the original image into blocks. In the invention designed to perform the area segmentation utilizing differences in brightness and texture between a cell image and a non-cell image other than the cell image, a preferable pixel size at the time of computation depends, for example, on the size of an object in an image such as a cell image. The pixel size for this purpose does not necessarily coincide with a preferable pixel size at the time of imaging. However, the pixel size can be individually optimized by converting the pixel size.

Further, it is also possible to provide, prior to classification, a step of receiving an instruction input by a user on a point belonging to the cell image and a point belonging to a background image in the original image and a step of obtaining a first feature amount and a second feature amount for each of at least one block including the point belonging to the cell image and at least one block including the point belonging to the background image based on a result of the input instruction and specifying a range of a cell cluster in a two-dimensional feature amount space based on the obtained results. According to such a configuration, the cell image and another area other than the cell image can be stably divided even if the type of the cell and imaging conditions are not fixed.

Further, the original image can be an image obtained by bright field imaging a cell. Since the cell is generally close to transparent and has a refractive index not much different from that of a culture medium, it is difficult to visually distinguish a cell image and a non-cell image in an image obtained by bright field imaging. By applying the invention to such an image, a cell area and other area(s) in the image can be satisfactorily and stably divided.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

INDUSTRIAL APPLICABILITY

The invention is applicable in biochemical and medical fields to image a cell and evaluate an image, and particularly preferable in technical fields requiring imaging free from such a processing as to damage a cultured cell.

REFERENCE SIGNS LIST 1 computer device
2 recording disk (recording medium)
B background
BL block
C cell
D debris
Ia original image

The invention claimed is:
1. An image processing method, comprising:
   obtaining an original image including a cultured cell image with a background image;
   dividing the original image into blocks each composed of a predetermined number of pixels and obtaining a spatial frequency component of an image in each block for each block;
   setting a total of intensities of low frequency components having a frequency equal to or lower than a predetermined frequency as a first feature amount, setting a total of intensities of high frequency components having a higher frequency than the low frequency component as a second feature amount, and classifying each block as the one belonging to a cell cluster corresponding to the cell or the one belonging to other than the cell cluster in a two-dimensional feature amount space composed of the first feature amounts and the second feature amounts;
   segmenting the original image into an area occupied by the blocks classified as the cell cluster and another area;
   receiving an instruction input by a user on a point belonging to the cell image and a point belonging to a background image in the original image;
   obtaining the first feature amount and the second feature amount for each of at least one block including the point belonging to the cell image and at least one block including the point belonging to the background image based on a result of the input instruction; and
   specifying a range of the cell cluster in the two-dimensional feature amount space based on obtained results,
   wherein an intensity of a direct-current component, out of the spatial frequency components, is set as the first feature amount and a total of intensities of all alternating-current components is set as the second feature amount.

2. The image processing method according to claim 1, wherein a two-dimensional discrete cosine transform is performed for each block based on pixel values of the pixels included in this block, and the intensity of each frequency component is obtained as a discrete cosine transform coefficient of this frequency component.

3. The image processing method according to claim 2, wherein each block is a square, a size of one side of which is equivalent to 4 pixels.

4. The image processing method according to claim 1, further comprising converting a pixel size of the original image from an original pixel size when the original image was obtained to a pixel size for block division different from the original pixel size prior to division of the original image into blocks.

5. The image processing method according to claim 1, wherein the original image is an image obtained by bright field imaging a cell.

6. The image processing method according to claim 1, wherein size of the block corresponds to size of one cell.

7. An image processing method, comprising:
  obtaining an original image including a cultured cell image with a background image;
  dividing the original image into blocks each composed of a predetermined number of pixels and obtaining a spatial frequency component of an image in each block for each block;
  setting a total of intensities of low frequency components having a frequency equal to or lower than a predetermined frequency as a first feature amount, setting a total of intensities of high frequency components having a higher frequency than the low frequency component as a second feature amount and classifying each block as the one belonging to a cell cluster corresponding to the cell or the one belonging to other than the cell cluster in a two-dimensional feature amount space composed of the first feature amounts and the second feature amounts; and
  segmenting the original image into an area occupied by the blocks classified as the cell cluster and another area, and
  prior to classification, receiving an instruction input by a user on a point belonging to the cell image and a point belonging to a background image in the original image, obtaining the first feature amount and the second feature amount for each of at least one block including the point belonging to the cell image and at least one block including the point belonging to the background image based on a result of the input instruction, and specifying a range of the cell cluster in the two-dimensional feature amount space based on obtained results,
  wherein a two-dimensional discrete cosine transform is performed for each block based on pixel values of the pixels included in this block, and the intensity of each frequency component is obtained as a discrete cosine transform coefficient of this frequency component, and
  wherein the two-dimensional discrete cosine transform is performed based on values obtained by subtracting an average pixel value of the entire original image from the pixel values of the respective pixels.

8. An image processing method, comprising:
  obtaining an original image including a cultured cell image with a background image;
  dividing the original image into blocks each composed of a predetermined number of pixels and obtaining a spatial frequency component of an image in each block for each block;
  setting a total of intensities of low frequency components having a frequency equal to or lower than a predetermined frequency as a first feature amount, setting a total of intensities of high frequency components having a higher frequency than the low frequency component as a second feature amount and classifying each block as the one belonging to a cell cluster corresponding to the cell or the one belonging to other than the cell cluster in a two-dimensional feature amount space composed of the first feature amounts and the second feature amounts; and
  segmenting the original image into an area occupied by the blocks classified as the cell cluster and another area, and
  prior to classification, receiving an instruction input by a user on a point belonging to the cell image and a point belonging to a background image in the original image, obtaining the first feature amount and the second feature amount for each of at least one block including the point belonging to the cell image and at least one block including the point belonging to the background image based on a result of the input instruction, and specifying a range of the cell cluster in the two-dimensional feature amount space based on obtained results,
  wherein a two-dimensional discrete cosine transform is performed for each block based on pixel values of the pixels included in this block, and the intensity of each frequency component is obtained as a discrete cosine transform coefficient of this frequency component, and
  wherein a total of intensities of a plurality of frequency components is obtained as a sum of absolute values of discrete cosine transform coefficients of the respective frequency components.

9. A non-transitory computer-readable recording medium having recorded thereon a program for performing the image processing method according to claim 1.

* * * * *